Figure 1:
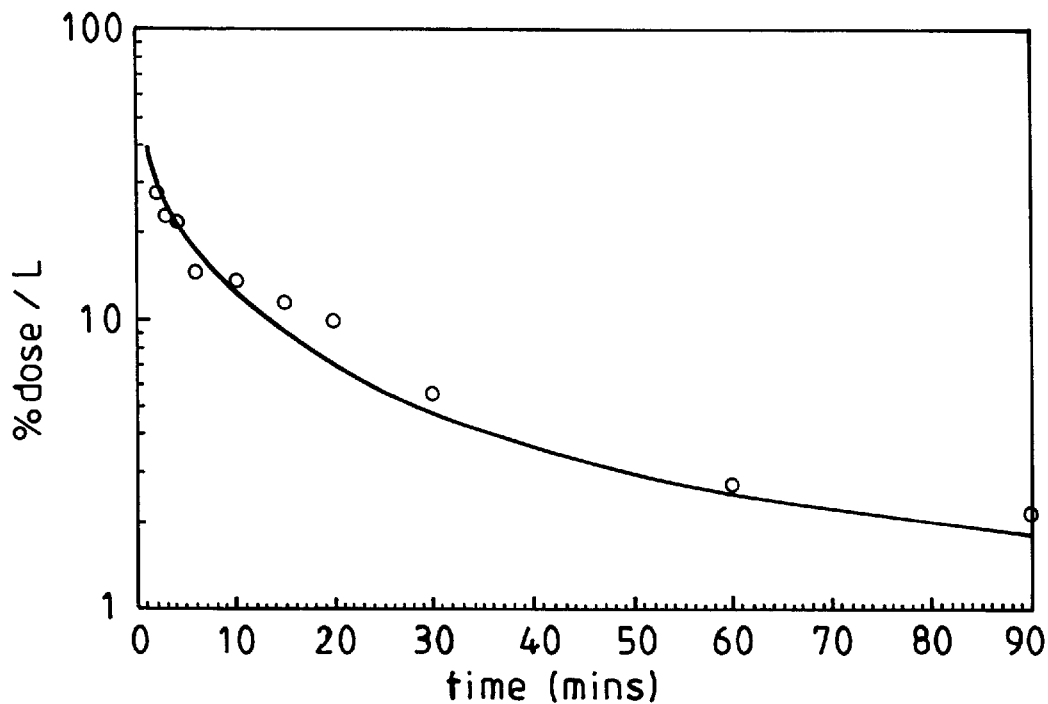

United States Patent [19]
Mills

[11] Patent Number: 6,030,841
[45] Date of Patent: Feb. 29, 2000

[54] LIVER FUNCTION TEST

[75] Inventor: Charles Oswald Mills, Birmingham, United Kingdom

[73] Assignee: Norgine Limited, United Kingdom

[21] Appl. No.: 09/032,325

[22] Filed: Feb. 27, 1998

[30] Foreign Application Priority Data

Aug. 12, 1997 [GB] United Kingdom ................... 9716962

[51] Int. Cl.⁷ .................................................. G01N 21/64
[52] U.S. Cl. .............................. 436/97; 436/172; 600/312
[58] Field of Search ............................ 436/172, 97, 177; 250/459.1, 461.1

[56] References Cited

U.S. PATENT DOCUMENTS

| 4,264,514 | 4/1981 | Hixson, Jr. et al. . |
| 4,848,349 | 7/1989 | Sherman et al. . |
| 5,154,176 | 10/1992 | Kanda ..................................... 128/633 |

FOREIGN PATENT DOCUMENTS

WO 9706829  2/1997  United Kingdom .

OTHER PUBLICATIONS

Plasma Clearance of Cholyl–Iysyl–fluorescein: a pilot study in humans, XP–002063326, *Journal of Hepatology*, 1997:27:1106–1109, P. Milkiewicz et al.

Physical and biological properties of fluroescent dansylated bile salt derivatives: the role of steroid ring hydroxylation, XP–000564384, Biochemiter et al, Biochemica et Biophysiker Acta, 1085 (1991), pp. 223–224, J. M. Crawford et al.

Conjugation (Detoxification) of $C^{1+}$—Labelled Cholic Acid in Human Liver Homogenates as a Test of Liver Function, XP–002063328, $10^{th}$ Symposium on Advances in Tracer Methodology, Mar. 25–26, 1965, P. H. Ekdahl et al.

Cholyllysyl Fluroscein and Related Lysyl Flurorescein Conjugated Bile Acid Analogues, C. O. Mills et al, *The Yale Journal of Biology and Medicine*, vol. 70, No. 4, pp. 447–457, Jul.–Aug. 1997.

Cholyl–Iysylfluroescein: snythesis, biliary excretion in vivo and during single–pass perfusion of isolated perfused rat liver, XP002082298, Database Chemabs, Chemical Abstracts Service, Columbus, Ohio & Biochim. Biophys. Acta (1991), 1115(2), 151–6 Coden: Bbacaq; Isnn: 0006–3002.

Biliary Lipid Output by Isolated Perfused Rat Livers in Response Tochoyl–Lysylfluorescein, XP000615216, BBA—Lipids and Lipid Metabolism, vol. 1256, No. 3, 1995, pp. 374–380, D. J. Baxter et al.

Synthesis, physical and biological properties of lithocholyl–lysyl–fluorescein: a fluorescent monohydroxy vile salt analogue with cholestatic properties, Biochimica et Biophysica Acta 1336 (1997), pp. 485–496, C. O. Mills et al.

*Primary Examiner*—Jeffrey Snay
*Attorney, Agent, or Firm*—Cantor Colburn LLP

[57] ABSTRACT

A method for the determination of liver function, comprises the steps of:

(i) introducing an effective amount of a coloured or fluorescent bile acid derivative intravenously into a patient, (ii) collecting samples of blood which has passed through the liver of the patient at timed intervals after step (i), and (iii) assessing the colour or fluorescence of bile acid derivative in each sample.

13 Claims, 1 Drawing Sheet

LIVER FUNCTION TEST

The present invention relates to a diagnostic agent for the determination of liver function (i.e. to enable identification of the nature of a liver disease in a patient to be determined), and to a method for such determination.

Uptake and biliary secretion of bile acids are important hepatic functions and an elevated concentration of serum bile acids is observed in several parenchymal and cholestatic liver diseases. Rapid clearance of natural [Korman et. al. New Eng. J. Med. (1975) 292, 1205] and radiolabelled [Horak et. al. Gastroenterology (1976) 71, 809] bile acids from plasma with a good correlation between impaired plasma clearance and hepatic dysfunction in patients with different liver diseases has been shown. However these methods entail complicated procedures and in the latter case the necessity of using radioactive compounds.

It is an object of the present invention, in at least one aspect, to provide a diagnostic agent for the determination of liver function in which the above disadvantages can be obviated or mitigated.

In a first aspect, the present invention resides in the use of a coloured or fluorescent bile acid derivative in the manufacture of a diagnostic agent for the determination of liver function, and in the use of a coloured or fluorescent bile acid derivative in a test for the determination of liver function performed on a blood sample.

The bile acid derivative preferably comprises a steroid moiety having an unblocked 3-hydroxyl, 7-hydroxyl or 12-hydroxyl substituent or any combination thereof, and an unblocked carboxyl group attached by means of an amide linkage to the side chain of the steroid moiety, and an active moiety which is to be targeted to the liver, said active moiety being attached to the α-carbon atom relative to the unblocked carboxyl group.

Preferably, said compound has the general formula (I):

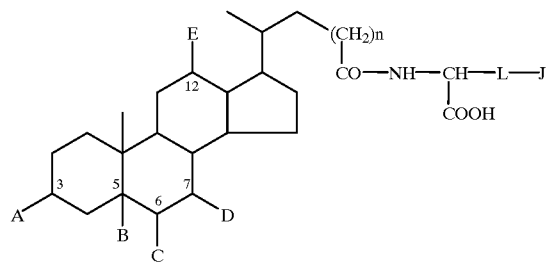

wherein A is α-OH or β-OH; B is α-H or β-H; C is -H, α-OH or β-OH; or B and C together form a double bond; D is -H, α-OH or ρ-OH; E is -H, α-OH or β-OH; L is a linking moiety; J is said coloured or fluorescent moiety; and n is 0 or 1.

Preferably, J is or includes a fluorescein, rhodamine or other fluorescing moiety.

The linking moiety is preferably N-terminated at its end attached to active moiety J, and L may be:
—$(CH_2)_n$NH, where n is 3 or 4,
—$(CH_2)_4$NH—$(CH_2)_3$NHC(=NH)NH—, or
—$(CH_2)_2$—CH(OH)$CH_2$NH—.

Alternatively, the moiety —NH—CH(COOH)-L- may be derived from S-adenosylhomocysteine, S-adenosylmethionine, S-amino-imadazole-4-carboxamide, asparagine, cadaverine, cystamine, citrulline, diaminopimelic acid, 2,4-diaminobutyric acid, cysteamine, glutamine, 3-hydroxykynurenine, kynurenine, putrescine or negamycin. Alternatively, acidic amino acids can be used instead of the above where active moiety J has one amino group and/or is hydrophobic. Preferably, the steroid moiety of the bile acid derivative is based on cholic acid, chenodeoxycholic acid, deoxycholic acid, hyodeoxycholic acid, hyocholic acid, α-, β- or ω-muricholic acid, nor-bile acids, lithocholic acid, 3β-hydroxycholenoic acid, ursodeoxycholic acid, allocholic acid (5α-cholan-24-oic-acid), or the like.

Most preferably, the fluorescent bile acid derivative is a cholyl-lysyl-fluorescein (CLF) having the formula:

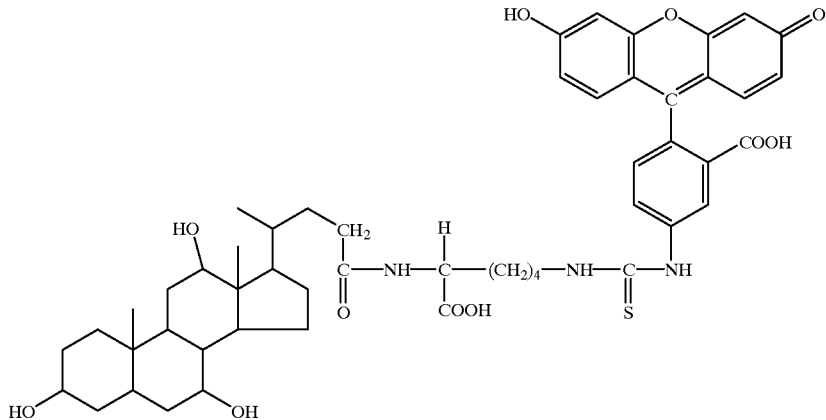

wherein the lysyl and fluorescein are linked by a thioamido moiety —C(S)NH—. This compound has in the past been referred to simply as "CLF", and "CLF" as used hereinafter is to be construed in this way.

In animal models, lysyl-fluorescein analogues of bile acids present several physical and physiological properties, including hepatic uptake [Saraswat et. al. Gut (1995) 36 (Suppl. 1), A18], which closely resemble those of natural bile acids.

In a second aspect, the invention resides in a method of analysing a blood sample containing a coloured or fluorescent bile acid derivative, comprising the steps of:
(i) processing the blood sample to obtain blood plasma containing the bile acid derivative,
(ii) measuring the colour or fluorescence of the bile acid derivative in the blood plasma, and
(iii) comparing the colour or fluorescence obtained in step (ii) with a standard.

Step (i) may be achieved by centrifugation of the sample.
Preferably, for a fluorescent bile acid derivative, step (i) additionally comprises separation of blood proteins from the plasma, for example by the addition of methanol to the plasma to precipitate the proteins, followed by centrifugation. If the blood proteins are not separated, they can complex with the fluorescent bile acid derivative and quench fluorescence, thereby giving artificially low and variable fluorescence measurements.

It may be desirable to include an additional step of diluting the plasma between steps (i) and (ii).

In a third aspect, the present invention resides in a method for the determination of liver function, comprising the steps of:
(i) introducing an effective amount of a coloured or fluorescent bile acid derivative intravenously into a patient,
(ii) collecting samples of blood which has passed through the liver of the patient at timed intervals after step (i), and
(iii) assessing the colour or fluorescence of bile acid derivative in each sample.

Preferably, step (iii) is effected by:
(a) processing the blood sample to obtain blood plasma containing the bile acid derivative,
(b) measuring the colour or fluorescence of the bile acid derivative in the blood plasma, and
(c) comparing the colour or fluorescence obtained in (b) with a standard.

Step (iii)(a) may be achieved by centrifugation of the sample.
Preferably, for a fluorescent bile acid derivative, step (iii)(a) additionally comprises separation of blood proteins from the plasma, for example by the addition of methanol to the plasma to precipitate the proteins, followed by centrifugation. If the blood proteins are not separated, they can complex with the fluorescent bile acid derivative and quench fluorescence, thereby giving artificially low and variable fluorescence measurements. It may be desirable to include an additional step of diluting the plasma between step (iii)(a) and (iii)(b).

More preferably, step (iii)(c) is effected by fitting the measurements obtained in step (iii)(b) to a plasma elimination curve, followed by a comparison of the plasma elimination curve with plasma elimination curves obtained from individuals having known liver function, to arrive at a determination of liver function for the patient.

Preferably, the coloured or fluorescent bile acid derivative is injected as a saline solution, the volume of said solution preferably being in the range of 1 cm$^3$ to 10 cm$^3$.

The dose is preferably at least 0.02 mg/Kg b.w. and preferably in the range of 0.02 to 0.5 mg/kg b.w.

Figure 2:
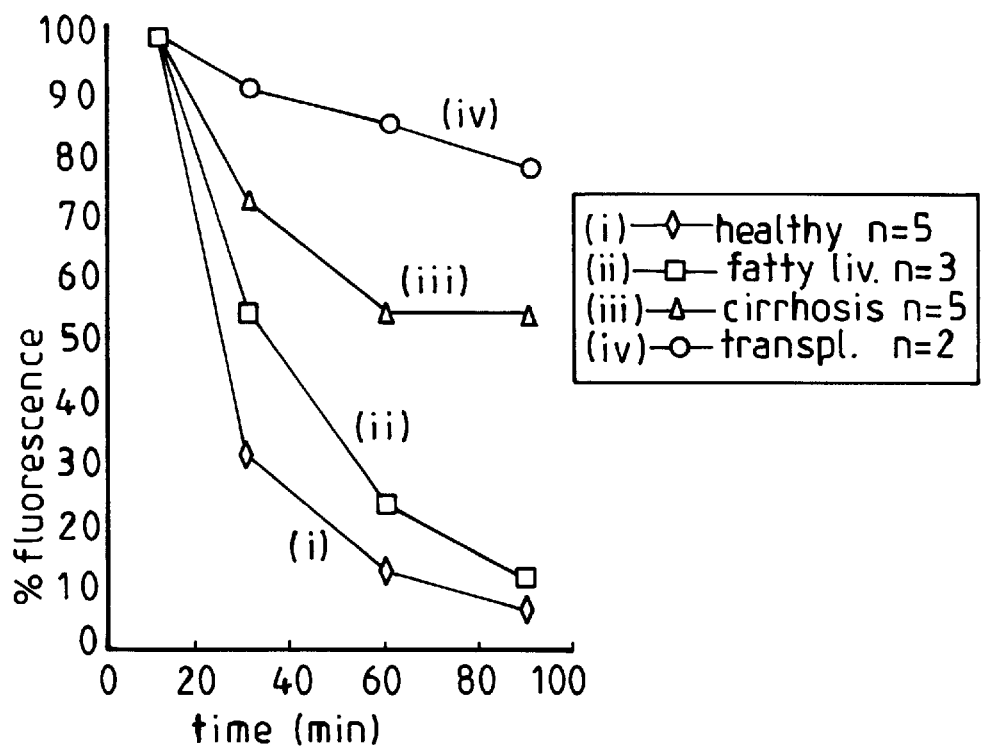

An embodiment of the invention will now be described by way of example with reference to the drawings, in which:

FIG. 1 shows a plasma elimination curve for cholyl-lysyl-fluorescein (CLF) in healthy volunteers, and FIG. 2 shows CLF plasma clearance curves for healthy patients and patients with with different causess of liver dysfunction.

CLF was synthesized as described elsewhere [Mills et. al. Biochim. Biophys. Acta (1991) 1115, 151], sterilized and tested for the presence of pyrogens.

A study was carried out in six healthy volunteers (1 female, 5 male), ages 30-53 years. Subjects were studied supine after overnight fasting. After an initial basal blood sample was taken, CLF in a dose of 0.02 mg/kg of body weight (b.w.) in physiological saline was injected intravenously during 15 seconds. Venous blood samples were collected from the opposite antecubital vein into gel and lithium heparin containers (sold under the Trade Name Vacutainers by Becton Dickinson Vacutainer Systems) at 2, 3, 4, 6, 10, 15, 20, 30, 60 and 90 minutes. The blood samples were then centrifuged and 0.5 ml aliquots of plasma were taken and added to 3.5 ml of methanol to precipitate plasma proteins, followed by further centrifugation. The supernatant (1 ml) was diluted to 3 ml with methanol and the fluorescence was then measured by spectrometer (Perkin Elmer LS5B Luminescence Spectrometer).

CLF concentration ($\mu$g/ml) was derived from a calibration curve which expressed the equation:

$$y=2566x-52.6$$

where y represents the measured fluorescence in fluorescence units at an excitation wavelength of 490 nm with emission at 520 nm and x represents the CLF concentration in $\mu$g/ml. The calibration curve was calibrated from fluorescence meaurements of solutions having known CLF concentrations followed by linear regression analysis.

Non linear plasma elimination curves presented as percentage dose administered per liter of plasma were fitted to a tri-exponential model. The half life ($t_{1/2}$ time) was calculated for the first ($t_{1/2\ 1st\ phase}$), second ($t_{1/2\ 2nd\ phase}$) and third ($t_{1/2\ 3rd\ phase}$) phases of the elimination curves from the equations:

$$t_{\frac{1}{2}\ 1st\ phase}=0.693/k_1\ t_{\frac{1}{2}\ 1st\ phase}=0.693/k_2\ t_{\frac{1}{2}\ 1st\ phase}=0.693/k_3$$

where $k_1$, $k_2$ and $k_3$ were calculated for each subject using the equation:

$$C_t=Ae^{-k_1t}+Be^{-k_2t}+Ce^{-k_3t}$$

in which:
$C_t$ is the concentration of CLF at time t,
A, B and C are the intercepts of each phase of elimination at t=0
$k_1$, $k_2$ and $k_3$ are fractional disappearance rates of the three phases of elimination.

The resulting plasma elimination curve is shown in FIG. 1.

There is extensive experience of exposure to the active moieties of CLF (cholyl-glycine and fluorescein) in humans. Cholyl-glycine is a naturally occurring primary bile salt in humans and intravenous fluorescein angiography is commonly performed in ophthalmology. Advantageously, the present invention allows the use of extremely small quantities of CLF. By comparison, the dose of glycocholate routinely employed in intravenous preparations such as Vit $K_1$ or Diazepam is approximately 300 times greater than the amount of CLF which may be used in the present invention and the dose of fluorescein applied in fundus fluorescein angiography is 400 times greater.

The plasma elimination curve for CLF showed three phases of elimination. $t_{1/2}$ for the first, second and third phases of elimination were 1.7±0.9 min, 6.7±1.6 min and 68±17 min respectively. Data for radiolabelled cholyl glycine reported by Cowen et. al. [Gastroenterology (1975) 68, 1567] gave $t_{1/2}$ for the first and the second exponentials as 1.7±0.1 and 7±0.1 min respectively. The cholyl glycine data were fitted to an elimination curve based on a bi-exponential model, but it is now thought to be more appropriate to apply a tri-exponential analysis [Engelking et. al. Clinical Science (1979) 57, 499]. Plasma retention of CLF at 90 minutes, when expressed as a percentage of the dose administered per liter of plasma was 2.2%.

In five healthy volunteers, a 25-fold higher dose of CLF (0.5 mg/kg b.w.) was injected in order to further assess the appropriateness of the dose chosen and the safety of the compound. Serum biochemistry including basic liver function tests, electrolytes and kidney function did not change significantly following this injection. Table. 1 shows values of standard liver function tests and plasma concentration of urea and creatinine before and after injection of the higher dose of CLF. Although there was a consistent diminution in plasma alkaline phosphatase levels post injection of CLF, this difference was not statistically significant (p=0.06).

TABLE 1

Tests of Liver Function Before And After CLF Dose of 0.5 mg/Kg b.w. For 5 Healthy Patients.

| test | before CLF injection | after CLF injection | difference |
| --- | --- | --- | --- |
| bilirubin ($\mu$M/L) | 10 | 11 | NS[3] |
| AST[1] (U/L) | 17 | 16 | NS |
| AlkP[2] (U/L) | 148 | 134 | p = 0.06 |
| Albumin (g/L) | 45 | 42 | NS |
| Urea (mM/L) | 4.4 | 4.3 | NS |
| Creatinine ($\mu$M/L) | 94 | 89 | NS |

[1]AST = aspartate aminotransferase
[2]AlkP = alkaline phosphatase
[3]NS = not significant Elimination curves obtained with the 25-fold increased dose confirmed that efficiency of hepatic clearance is unchanged. This reflects the behaviour of natural bile acids observed by Korman et. al. (referred to above). However, doses of CLF used in the present invention are much lower than the doses of natural bile acid utilized by Korman et. al. (0.02–0.5 mg/kg b.w. versus 5 mM/kg b.w. which equates to ≈2.4 g/Kg b.w.). The volume of distribution of CLF calculated as proposed by Thiordleifsson et. al. [Gut (1977) 18, 697] at 2214±147 ml, was similar to values for radiolabelled cholyl glycine reported by others [Gilmore et. al. Gut (1978) 19, 1110].

The above results were also calculated in terms of the fluorescence at 60 min compared with the fluorescence at 10 min, expressed as a percentage. For radiolabelled cholic acid (Horak et. al., referred to above), this gave 60 min plasma retention of 8±1% for healthy volunteers compared to 71% for patients with fulminant hepatic failure (FHF) who subsequently died and 60% for FHF patients who survived (the difference between the two groups being statistically significant). The percentage of fluorescence after 60 min of 13.1±1.6% for the present invention was similar to the data obtained for the healthy volunteers in Horak's work. The body of data showing that CLF plasma elimination is very similar to the elimination of natural bile acids suggests that there will be significant differences in plasma clearance of CLF between healthy individuals and those with liver dysfunction. This is confirmed by the data shown in FIG. 2. The elimination curves of FIG. 2 show differing rates of CLF elimination for (i) healthy patients, and patients with (ii) fatty, (iii) cirrhotic and (iv) recently transplanted livers (5 days post operation). Thus, not only does the present invention offer a useful means for determining liver function in a patient, it may also enable the cause of any dysfuncion to be diagnosed.

What I claim is:

1. A method of determining the liver function of a patient, comprising:

processing a series of blood samples which have passed through the liver of the patient and which have been collected at timed intervals after introducing an effective amount of a colored or fluorescent bile acid derivative intravenously into the patient;

assessing the color or fluorescence of bile acid derivative in each sample by:

processing the blood sample to obtain blood plasma containing the bile acid derivative, and measuring the color or fluorescence of the bile acid derivative in the blood plasma; and fitting the measurements obtained in the measuring of the color or fluorescence of the bile acid derivative in the blood plasma to a plasma elimination curve and comparing the plasma elimination curve with plasma elimination curves obtained from individuals having known liver function, to arrive at a determination of liver function for the patient.

2. A method as claimed in claim 1, further including the step of diluting the plasma between step (iii)(a) and (iii)(b).

3. A method as claimed in claim 1, wherein step (iii)(a) is effected by centrifugation of the sample.

4. A method as claimed in claim 3, wherein a fluorescent bile acid derivative is employed and step (iii)(a) additionally comprises separation of blood proteins from the plasma before followed by centrifugation.

5. The method as claimed in claim 1, wherein the bile acid derivative comprises (a) a steroid moiety having (i) at least one unblocked substituent selected from the group consisting of an unblocked 3-hydroxyl substituent, an unblocked 7-hydroxyl substituent and an unblocked 12-hydroxyl substituent, and (ii) an unblocked carboxyl group attached by means of an amide linkage to a side chain of the steroid moiety; and (b) an active moiety which is to be targeted to the liver, said active moiety being attached to an α-carbon atom relative to the unblocked carboxyl group.

6. A method as claimed in claim 5, wherein the steroid moiety of the bile acid derivative is based on an acid selected from the group consisting of cholic acid, chenodeoxycholic acid, deoxycholic acid, hyodeoxycholic acid, hyocholic acid, α-, β- or ω-muricholic acid, norbile acids, lithocholic acid, 3β-hydroxycholenoic acid, ursodeoxycholic acid and allocholic acid (5α-cholan-24-oic-acid).

7. A method as claimed in claim 5, wherein the fluorescent bile acid derivative is a cholyl-lysyl-fluorescein (CLF) having the formula:

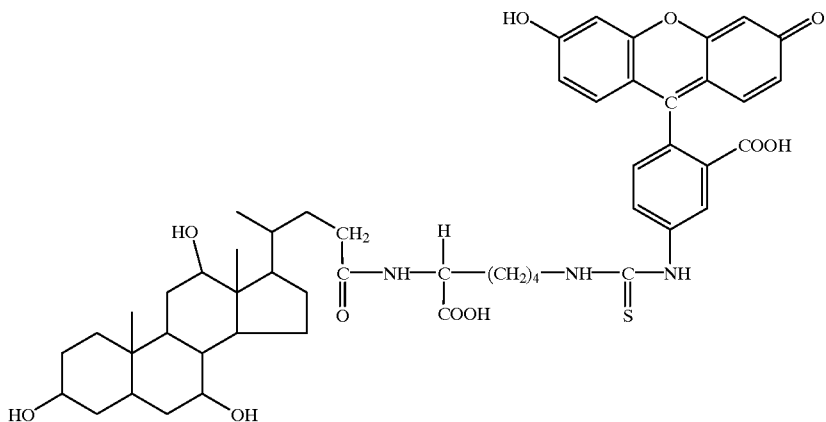

wherein the lysyl and fluorescein are linked by a thioamido moiety —C(S)NH—.

8. A method as claimed in claim 1; wherein said derivative has the general formula (I):

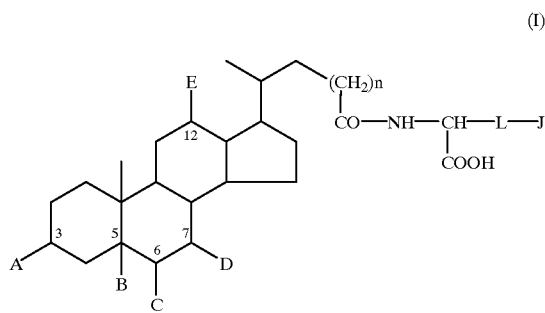

(I)

wherein A is selected from the group consisting of α-OH and β-OH; B is selected from the group consisting of α-H and β-H; C is selected from the group consisting of -H, α-OH and β-OH; or B and C together form a double bond; D is selected from the group consisting of -H, α-OH and β-OH; E is selected from the group consisting of -H, α-OH and β-OH; L is a linking moiety; J is said coloured or fluorescent moiety; and n is 0 or 1.

9. A method as claimed in claim 8, wherein j is or includes a fluorescein, rhodamine or other fluorescing moiety.

10. A method as claimed in claim 8, wherein the linking moiety L is N-terminated at its end attached to active moiety J, and L is selected from the group consisting of:

—(CH$_2$)$_n$NH, where n is 3 or 4,

—(CH$_2$)$_4$NH—(CH$_2$)$_3$NHC(=NH)NH—, and

—(CH$_2$)$_2$—CH(OH)CH$_2$NH—.

11. A method as claimed in claim 8, wherein the moiety-NH—CH(COOH)-L- in the general formula (I) is derived from a compound selected from the groupconsisting of S-adenosylhomocysteine, S-adenosylmethionine, S-aminoimadazole-4-carboxamide, asparagine, cadaverine, cystamine, citrulline, diaminopimelic acid, 2,4-diaminobutyric acid, cysteamine, glutamine, 3-hydroxykynurenine, kynurenine, putrescine and negamycin.

12. A method of determining the liver function of a patient, comprising:

processing a blood sample which has passed through the liver of the patient and which has been collected at a predetermined time interval after introducing an effective amount of a colored or fluorescent bile acid derivative intravenously into the patient; and assessing the color or fluorescence of the bile acid derivative in the sample by:

processing the blood sample to obtain blood plasma containing the bile acid derivative, measuring the color or fluorescence of the bile acid derivative in the blood plasma, and comparing the measurement obtained in measuring the color or fluorescence of the bile acid derivative in the blood plasma with at least one standard so as to arrive at a determination of liver function for the patient.

13. A method as claimed in claim 12, wherein step (i) is achieved by centrifugation of the sample.

* * * * *